US005486202A

United States Patent [19]
Bradshaw

[11] Patent Number: 5,486,202
[45] Date of Patent: Jan. 23, 1996

[54] CARDIAC STIMULATOR LEAD CONNECTOR

[75] Inventor: James I. Bradshaw, Surfside, Tex.

[73] Assignee: Intermedics, Inc., Angleton, Tex.

[21] Appl. No.: 169,673

[22] Filed: Dec. 17, 1993

[51] Int. Cl.6 ................................................. A61N 1/372
[52] U.S. Cl. ........................................................ 607/37
[58] Field of Search ................................... 128/639, 641, 128/642; 607/1, 2, 37, 119; 439/817, 819

[56] References Cited

U.S. PATENT DOCUMENTS

| 4,860,750 | 8/1989 | Frey et al. | 128/419 |
| 4,942,876 | 7/1990 | Gotthardt | 607/37 |
| 5,069,209 | 12/1991 | Posin | 607/37 |
| 5,275,620 | 1/1994 | Darby et al. | 607/1 |
| 5,413,595 | 5/1995 | Stutz, Jr. | 607/37 |
| 5,433,734 | 7/1995 | Stokes et al. | 607/37 |

FOREIGN PATENT DOCUMENTS

| 0342392 | 11/1989 | European Pat. Off. | 607/37 |
| 0357941 | 3/1990 | European Pat. Off. | 607/37 |
| 3636158 | 4/1987 | Germany. | |
| 3718913 | 12/1988 | Germany | 607/37 |
| 8905170 | 6/1989 | WIPO. | |

Primary Examiner—Krista M. Zele
Attorney, Agent, or Firm—Richard L. Robinson

[57] ABSTRACT

A connector terminal in a cardiac stimulator for receiving a connector pin of an associated lead includes a hollow box member having opposite end walls defining a first bore for receipt of the connector pin. A ring member movably disposed within the box member defines a second bore generally aligned with the first bore for also receiving the connector pin. A threaded neck connected to the ring member extends perpendicular to the second bore and is received within a through bore of the box member that is disposed perpendicular to the first bore. An internally threaded cap threadedly engages the threaded neck and bears in a thrust bearing relationship on the box portion. As the cap is rotated, the ring portion is drawn upwardly as the cap presses downwardly on the box portion, causing the second bore to be moved transversely out of alignment with the first bore. A connector pin received through both first and second bores is clamped therebetween and retained against axial withdrawal from the connector terminal.

12 Claims, 3 Drawing Sheets

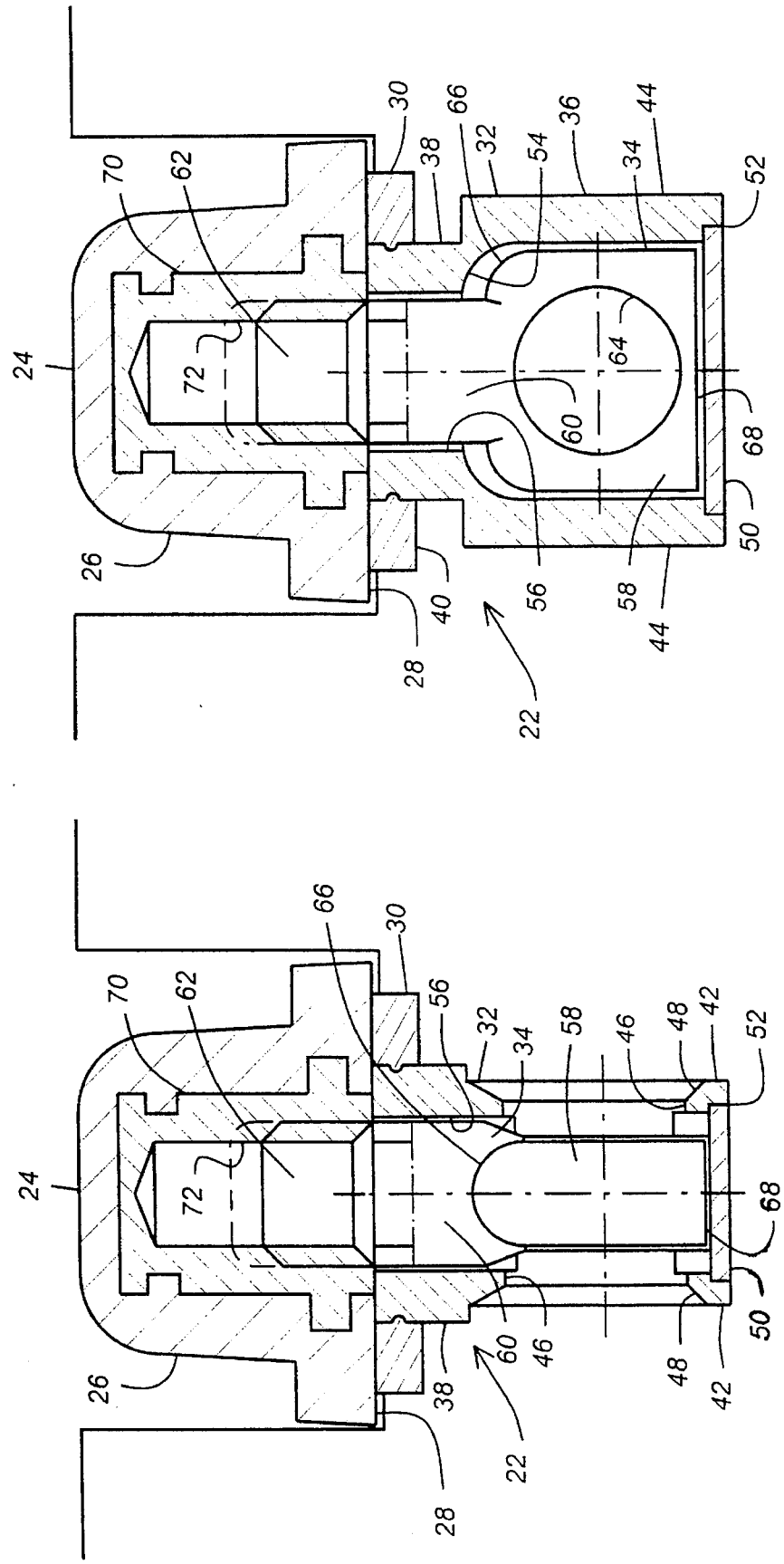

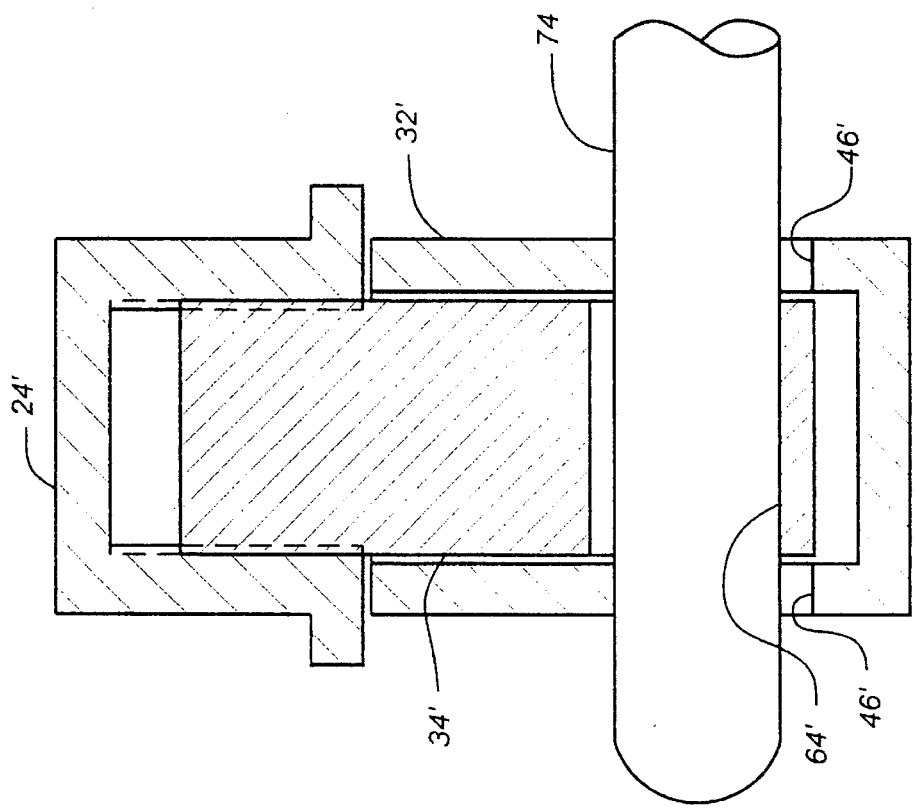
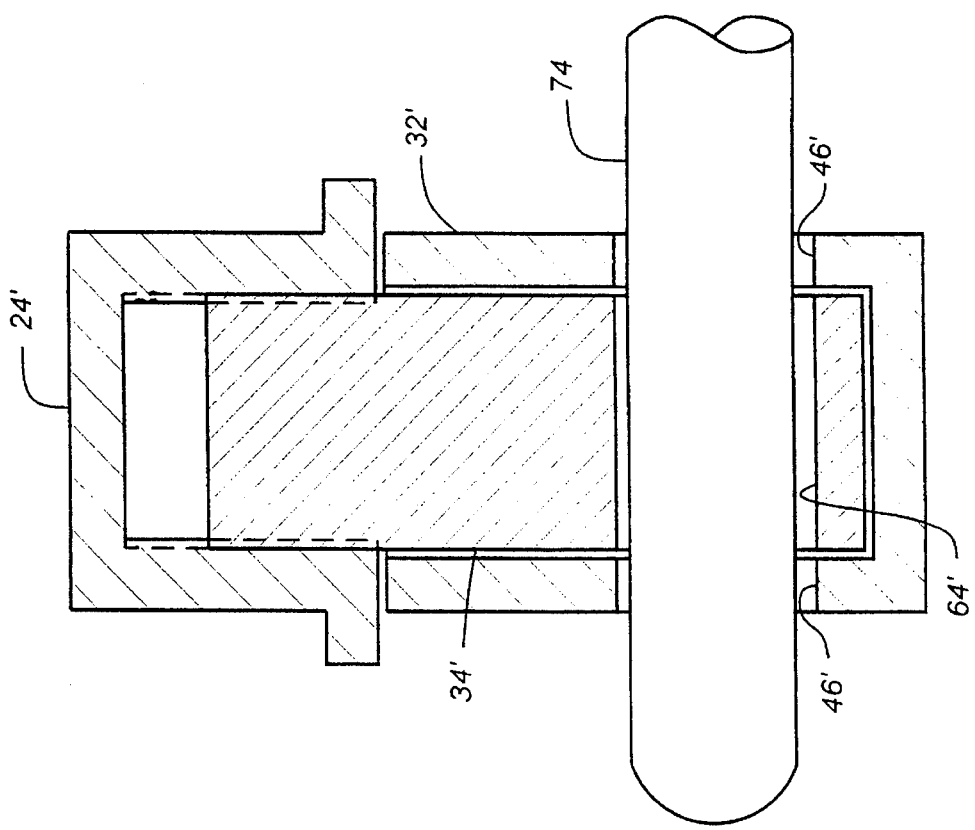

CARDIAC STIMULATOR LEAD CONNECTOR

BACKGROUND OF THE INVENTION

1. Field of the Invention

The present invention relates to a connector in a header of an implantable cardiac stimulator for coupling to a lead for conducting electrical signals between the cardiac stimulator and the heart.

2. Background Information

Implantable cardiac stimulators, including pacemakers, anti-tachycardia pacers, and defibrillators are used to artificially stimulate cardiac tissue with an electrical signal in order to correct or modify the rhythm of the heart. Implantable cardiac stimulators generally comprise a housing or can which hermetically encloses a battery and electronic circuitry for sensing electrical signals generated by the heart and for generating therapeutic electrical stimulating signals to be delivered to the heart. The housing is generally implanted subcutaneously. A lead having one or more electrodes at one end is implanted in the heart via an endovascular route so that the electrode is lodged in a selected chamber of the heart. The other end of the lead has a connector pin which is mechanically and electrically coupled to the cardiac stimulator.

It is important that the lead be safely secured to the cardiac stimulator to prevent it from being inadvertently decoupled. Since cardiac stimulators must be removed and replaced at the end of the useful life of the battery, preferably without disturbing the electrode, the lead connection must also be readily disconnectable.

It is known in the art to accomplish the connection by inserting an exposed connector pin of the lead into an electrical terminal located at the inboard end of a cylindrical bore in a header of the cardiac stimulator. The lead is then fixed in place by use of a setscrew, which extends through a hole in the side of the header and is received in a threaded hole in the electrical terminal. The setscrew is tightened until it bears against the side of the connector pin.

This conventional technique for securing the lead to the pacer has some disadvantages. The setscrew is extremely small and can be lost if it is inadvertently backed out too far. Also, the setscrew makes point contact with the connector pin of the lead, which can result in significant deformation of the connector pin if the set screw is over tightened, which can in turn make it difficult to disconnect the connector pin from the header of the cardiac stimulator.

It would be desirable to provide a connector in a cardiac stimulator for receiving a connector pin of a lead wherein the means for engaging the connector pin cannot be inadvertently lost. It would also be desirable to provide such a connector that is configured to alleviate the problem of deformation of the connector pin. These and other desirable goals are achieved by the present invention.

SUMMARY OF THE INVENTION

In accordance with one aspect of the invention, an implantable cardiac stimulator includes a connector for receiving and retaining an electrical connector pin of an electrical lead adapted for conducting electrical signals between the cardiac stimulator and cardiac tissue. The connector includes a first member having a first bore sized to receive the connector pin. A second member has a second bore also sized to receive the connector pin. The second member is movable relative to the first member between a first orientation in which the second bore is axially aligned with the first bore, and a second orientation in which the second bore is offset transversely relative to the second bore. Manipulable means are provided for engaging the first and second members for causing the second member to move between the first and second orientations such that a connector pin disposed within each of the first and second bores is urged transversely by the second bore against the first bore and thereby frictionally engaged by the first and second bores to retain the connector pin against axial withdrawal from the bores.

In accordance with another aspect of the invention, a method is provided for receiving and retaining in a cardiac stimulator an electrical connector pin of an electrical lead adapted for conducting electrical signals between the cardiac stimulator and cardiac tissue. The method includes the steps of providing in the cardiac stimulator a first connector member having a first bore sized to receive the connector pin, and providing in the cardiac stimulator a second connector member having a second bore sized to receive the connector pin. The first and second bores are aligned. The connector pin is received within both of the first and second bores, and the second connector member is moved relative to the first connector member in a direction transverse to the bores such that the connector pin is frictionally retained against axial withdrawal from the bores.

It is an object of the present invention to provide an improved connector terminal for an implantable cardiac stimulator for receiving a connector pin of a lead, wherein the means for engaging the connector pin cannot be inadvertently lost. It is a further object of the invention to provide such a connector that is configured to alleviate the problem of deformation of the connector pin.

Other objects and advantages of the present invention will be apparent from the following description of a preferred embodiment made with reference to the drawings.

BRIEF DESCRIPTION OF THE DRAWINGS

FIG. 3 is an enlarged cross-sectional view of the connector of FIG. 2.

FIG. 4 is another enlarged cross-sectional view of the connector of FIG. 2 viewed axially with respect to the connector bore.

FIG. 5 is a stylized illustration of a connector constructed in accordance with the principles of the present invention, with a connector pin received therein.

FIG. 6 is a stylized illustration of the connector of FIG. 5, showing the connector pin clamped therein.

DETAILED DESCRIPTION OF A PREFERRED EMBODIMENT

Figure 1:
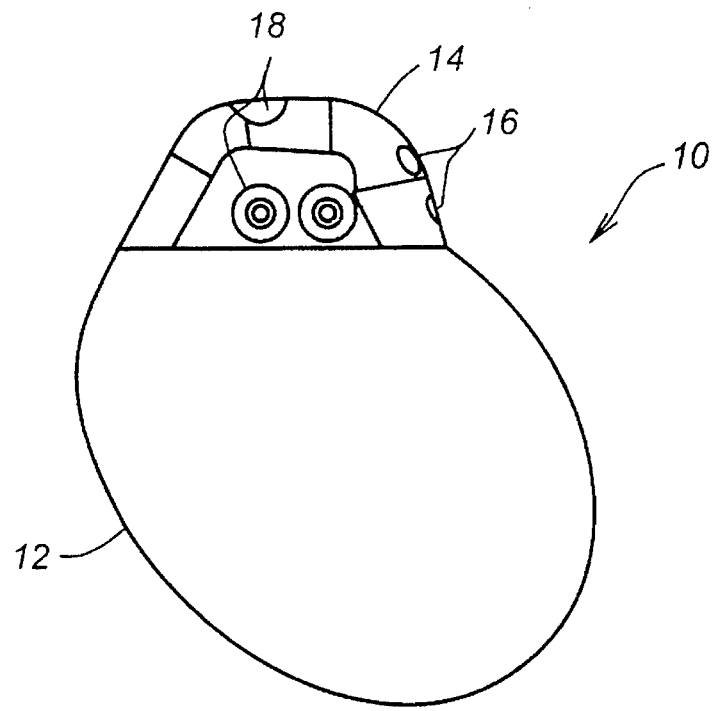
FIG. 1 is a side view of a cardiac stimulator incorporating a connector configured in accordance with the present invention.

Referring to FIG. 1, there is illustrated an implantable cardiac stimulator 10 having a titanium housing or "can" 12, and a cast epoxy header 14. Embedded within header 14 are a plurality of electrical connector terminals each aligned with a respective receptacle bore 16 for receipt of a connector pin of an associated conventional lead. Associated with each connector terminal and its respective receptacle bore is an access port 18 through which manipulable means for securing the connector pin to the connector terminal is accessible.

Figure 2:
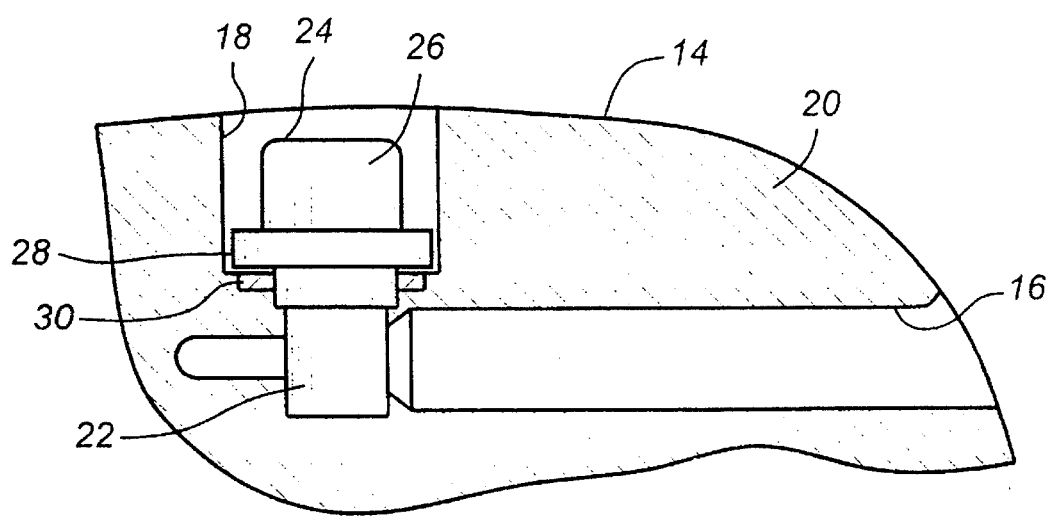
FIG. 2 is an enlarged cross-sectional view of a portion of the header of the cardiac stimulator of FIG. 1 showing the connector of the present invention.

Referring now to FIG. 2, a portion of header 14 is shown enlarged and in cross-section. Embedded within epoxy 20 is a metal connector terminal 22 which is electrically connected via a wire and insulated feedthrough (not shown) to electronic circuitry inside housing 12. Connector terminal 22 communicates with the exterior of cardiac stimulator 10 through cylindrical receptacle bore 16. An electrically insulative plastic cap 24 disposed within access port 18 has a fluted exterior surface 26 for engagement with an interiorly fluted tool that can be used to rotate cap 24, as explained further below. Cap 24 has a flanged rim 28 that engages and seals against an elastomeric gasket 30 to prevent electrical contact between connector terminal 22 and bodily fluid that is present in access port 18 after implantation of cardiac stimulator 10 in the body.

Referring to FIGS. 3 and 4, connector terminal 22 is shown in greater detail. Connector terminal 22 is comprised of a first element 32 and a second element 34 disposed within first element 32 and movable relative thereto.

First element 32 includes a generally rectangular hollow box portion 36 having a cylindrical collar 38 extending therefrom. Collar 38 includes an annular groove 40 thereabout for receiving a corresponding annular protrusion on the inner diameter of gasket 30 to hold gasket 30 in place. Box portion 36 of first element 32 has opposite end walls 42 and opposite side walls 44. Each end wall 42 is penetrated by a first bore 46 having a chamfered opening 48. Bottom wall 50 of box portion 36 is laser welded thereto about its periphery 52 after second element 34 is inserted within first element 32 through the bottom of box portion 36. Box portion 36 also includes a top wall 54 located on opposite sides of collar 38 at the transition from side wall 44 to collar 38. Collar 38 has a cylindrical through bore 56 that communicates with the hollow interior of box portion 36.

Second element 34 includes a ring portion 58 disposed within the hollow interior of box portion 36 of first element 32, and a cylindrical neck portion 60 that is disposed within through bore 56 of collar 38 of first element 32. Neck portion 60 has an externally threaded portion 62. Ring portion 58 has a second bore 64 therethrough that is of substantially the same diameter as first bore 46 and generally axially aligned therewith. Ring portion 58 also includes a shoulder 66 disposed on opposite sides of neck portion 60 and generally adjacent top wall 54 of box portion 36. Ring portion 58 is dimensionally smaller than the hollow interior of box portion 36 and is therefore free to move somewhat in the axial direction of through bore 56. Sufficient clearance is provided between the bottom 68 of ring portion 58 and bottom wall 50 of box portion 36 that second bore 64 can be displaced downwardly out of axial alignment with first bore 46. Likewise, sufficient clearance is provided between shoulder 66 of ring portion 58 and top wall 54 of box portion 36 that second bore 64 can be displaced upwardly out of axial alignment with first bore 46. Of course, there exists an intermediate position for ring portion 58 relative to box portion 36 in which second bore 64 is aligned with first bore 46.

Plastic cap 24 is molded about a metal sleeve 70 having an internally threaded bore 72 in threaded engagement with threaded portion 62 of neck portion 60. Sleeve 70 has an annular end face that abuts and engages an annular end face of collar 38 in a thrust bearing relationship. As cap 24 is rotated about its axis using an appropriate tool in engagement with fluted surface 26, interengaged threads 62 and 72 cause second element 34 to move axially up or down relative to first element 32, depending on the direction of rotation and the "handedness" of the threads. Preferably, the threads are arranged such that clockwise rotation of cap 24 as viewed from above results in second element 34 being drawn upwardly relative to first element 32 as sleeve 70 presses down against collar 38.

Referring to FIGS. 5 and 6, the operation of connector terminal 22 is illustrated by way of stylized representations of the preferred embodiment described above that have been simplified for clarity. Components in FIGS. 5 and 6 that correspond to elements of the preferred embodiment described above are designated by like primed reference numerals.

With particular reference to FIG. 5, second element 34' is shown positioned relative to first element 32' such that second bore 64' is axially aligned with first bore 46'. A connector pin 74 of a lead is shown received through both bore 46' and bore 64'.

Referring now to FIG. 6, cap 24' has been rotated relative to the threaded neck of second element 34' such that cap 24' presses down on first element 32' and draws second element 34' upwardly. Consequently, second bore 64' is displaced upwardly and engages the bottom side of connector pin 74, thereby urging the top side of connector pin transversely into engagement with first bore 46'. Connector pin 74 is placed in shear stress between bores 46' and 64'. Sufficient friction is generated by the engagement of the surface of connector pin 74 and the respective opposite surfaces of bores 46' and 64' that connector pin 74 cannot be axially withdrawn from connector terminal 22' by ordinary forces to which it may be subjected during use.

Connector pin 74 can be easily withdrawn from connector terminal 22' by rotating cap 24' in the opposite direction so as to release the tension on second element 34' and allow second bore 64' to resume axial alignment with first bore 46'. Because the transverse loading applied to connector pin 74 by bores 46' and 64' are spread over a relatively large surface area, as opposed to a set screw which applies a point load, sufficient frictional holding power is generated without undue deformation of connector pin 74. Consequently, the ability to withdraw connector pin 74 from connector terminal 22' is less likely to be inhibited by deformation of the connector pin than in the prior art.

While the present invention has been illustrated and described with particularity in terms of a preferred embodiment, it should be understood that no limitation of the scope of the invention is intended thereby. The scope of the invention is defined only by the claims appended hereto. It should also be understood that variations of the particular embodiment described herein incorporating the principles of the present invention will occur to those of ordinary skill in the art and yet be within the scope of the appended claims.

What is claimed is:

1. In an implantable cardiac stimulator, a connector for receiving and retaining an electrical connector pin of an electrical lead adapted for conducting electrical signals between said cardiac stimulator and cardiac tissue, said connector comprising:

a first member having a first bore sized to receive said connector pin;

a second member having a second bore sized to receive said connector pin, said second member being movable relative to said first member between a first orientation in which said second bore is axially aligned with said first bore, and a second orientation in which said second bore is offset transversely relative to said second bore; and manipulable means engaging said first and second members for causing said second member to move between said first and second orientations in response to manipulation of said manipulable means, such that a connector pin disposed within each of said first and second bores is urged transversely by said second bore against said first bore and thereby frictionally engaged by said first and second bores to retain said connector pin against axial withdrawal from said bores, said manipulable means comprising threaded means for engaging one of said first and second members in threaded relationship.

2. The implantable cardiac stimulator of claim 1, in which said first member includes a box member having a hollow interior and opposite end walls defining said first bore, and said second member is disposed within the hollow interior such that said second bore of said second member is disposed between said opposite end walls.

3. The implantable cardiac stimulator of claim 2, in which said first member includes a through bore oriented perpendicular to said first bore and communicating with said first bore, and said second member includes a neck portion oriented perpendicular to said second bore and disposed within said through bore.

4. The implantable cardiac stimulator of claim 3, in which said neck portion of said second member is threaded, and said manipulable means includes an internally threaded cap in threaded engagement with said neck portion and disposed in thrust bearing relationship with said first member.

5. The implantable cardiac stimulator of claim 4, in which said box portion includes a top wall and said second member includes a shoulder adjacent said top wall whereby abutment of said shoulder against said top wall precludes withdrawal of said second member from said first member.

6. The implantable cardiac stimulator of claim 1, in which said manipulable means further engages one of said first and second members in a thrust bearing relationship.

7. The implantable cardiac stimulator of claim 6, in which said manipulable means engages said second member in said threaded relationship and engages said first member in said thrust bearing relationship.

8. The implantable cardiac stimulator of claim 7, in which said first member includes a through bore oriented perpendicular to said first bore and communicating with said first bore, and said second member includes a neck portion oriented perpendicular to said second bore and disposed within said through bore.

9. The implantable cardiac stimulator of claim 8, in which said neck portion of said second member is threaded, and said threaded means of said manipulable means includes an internally threaded cap in threaded engagement with said neck portion and disposed in thrust bearing relationship with said first member.

10. The implantable cardiac stimulator of claim 9, in which said first member includes a collar having an annular end face circumscribing said through bore, said cap being disposed in said thrust bearing relationship with said annular end face.

11. A method for receiving and retaining in a cardiac stimulator an electrical connector pin of an electrical lead adapted for conducting electrical signals between said cardiac stimulator and cardiac tissue, said method comprising the steps of:

providing in said cardiac stimulator a first connector member having a first bore sized to receive said connector pin;

providing in said cardiac stimulator a second connector member having a second bore sized to receive said connector pin;

providing in said cardiac stimulator manipulable means engaging said first and second members for retaining said connector pin against axial withdrawal from said bores, said manipulable means engaging one of said first and second members in threaded relationship;

aligning said first and second bores;

receiving said connector pin within both of said first and second bores; and manipulating said manipulable means to threadedly move said manipulable means relative to said one of said first and second members while said manipulable means engages another of said first and second members to move said second connector member relative to said first connector member in a direction transverse to said bores such that said connector pin is frictionally retained against axial withdrawal from said bores.

12. The method of claim 11 in which said manipulating step is performed such that said connector pin is frictionally retained without substantially deformation of said connector pin.

* * * * *